United States Patent [19]

Gazzaniga et al.

[11] Patent Number: 4,689,218
[45] Date of Patent: Aug. 25, 1987

[54] EFFERVESCENT COMPOSITION WITH ANALGESIC ACTIVITY

[75] Inventors: Annibale Gazzaniga, Rescaldina, Italy; Valter Gianesello, Vacallo, Switzerland; Federico Stroppolo, Pregassona, Switzerland; Luigi Vigano', Lugano, Switzerland

[73] Assignee: Zambon S.p.A., Vicenza, Italy

[21] Appl. No.: 927,448

[22] Filed: Nov. 6, 1986

[30] Foreign Application Priority Data

Nov. 12, 1985 [IT] Italy ............................... 22800 A/85

[51] Int. Cl.4 ..................... A61K 9/00; A61K 31/19; A61K 31/195
[52] U.S. Cl. ..................................... 424/43; 514/557; 514/561
[58] Field of Search ................... 514/557, 561; 424/43

[56] References Cited

U.S. PATENT DOCUMENTS 4,569,937 2/1986 Baker et al. ......................... 514/557
4,593,044 6/1986 Metz ................................... 514/557

OTHER PUBLICATIONS

Chem. Abst. 97(1982) 61070x.

Primary Examiner—Stanley J. Friedman
Attorney, Agent, or Firm—Stevens, Davis, Miller & Mosher

[57] ABSTRACT

It is described an effervescent composition consisting of:
Ibuprofen 9–17% w/w
Arginine 17–33% w/w
Sodium or potassium bicarbonate 20–35% w/w
Sodium bitartrate 25–40% w/w Such composition is useful for pharmaceutical preparations in the form of effervescent tablets or granulates.

21 Claims, No Drawings

EFFERVESCENT COMPOSITION WITH ANALGESIC ACTIVITY

The present invention relates to a pharmaceutical composition with analgesic activity and, more particularly, it relates to a pharmaceutical effervescent composition containing Ibuprofen as active ingredient and useful for the preparation of effervescent tablets or granulates.

Ibuprofen [2-(4-isobutyl-phenyl)-propionic acid] is a physically well-tolerated drug with analgesic and antiinflammatory activity (Merck Index, 10th Edition, No. 4797) which yet shows two disadvantages constituted by some irritability of gastric mucosa and by a relatively slow kinetics of absorption which is the cause of a delay in showing the analgesic effect.

These unfavourable factors come out especially when the drug is administered by oral route in the form of a tablet.

Besides, the administration of the drug as an aqueous suspension is not suitable in that it has a very bitter taste and it is irritant for the mucosa of the mouth.

In theory it is possible to overcome these problems by administering an aqueous solution of the drug, yet Ibuprofen has a very low solubility in water and the solubilization of its salts in a reasonable volume of water needs long periods of time and heating, such operations being not compatible with the use of an analgesic carried out directly by the patient himself.

In a way similar to that realized for other drugs with the same kind of activity, for example acetylsalicylic acid, it has been thought then to prepare effervescent tablets which could ensure a fast solubilization of the drug.

Nevertheless the usual effervescent preparations suitable in pharmaceutical technology did not give the desired effect, as Ibuprofen resulted still very little soluble with the formation of crystals of the drug on the bottom or on the inside walls of the glass in which the drug has been dissolved.

We have now surprisingly found an effervescent composition which overcomes all the above discussed unfavourable features and which can be used for the preparation of effervescent tablets or granulates with an easy and immediate use.

The composition according to the present invention consists of

Ibuprofen 9–17% w/w
Arginine 17–33% w/w
Sodium or potassium bicarbonate 20–35% w/w
Sodium bitartrate 25–40% w/w
the whole being 100%.

Preferably the weight ratio between Ibuprofen and Arginine is about 1:1.9.

The composition object of the present invention is peculiar in its components. Particularly, the most binding factor is the use of sodium bitartrate (tartaric acid monosodium salt) as an acid agent able to develop carbon dioxide from bicarbonate.

Surprisingly, the commonly used acids for the preparation of effervescent tablets (Pharmaceutical Dosage Forms—Tablets, vol. 1, edited by H. A. Lieberman, L. Lachman—Marcel Dekker, Inc.—New York and Basel) such as citric acid, tartaric acid, monosodium citrate, sodium citrate and others, showed to be unsuitable as, already during the phase of effervescence, it was possible to observe the formation of precipitates essentially consisting of Ibuprofen (see example 6).

Sodium or potassium bicarbonate could be substituted by the corresponding carbonates or by sodium glycine-carbonate, but with no practical and economic advantage.

Instead of sodium bitartrate, potassium bitartrate as well could be use but the latter is difficult to be found on the market in industrial amounts.

Arginine is another essential factor for the solubilization of Ibuprofen.

If desired it is possible to substitute a portion of arginine (up to 30–40% at the most) with lysine.

Nevertheless larger amounts of lysine make unacceptable the composition from the pharmaceutical point of view since lysine easily degrades making of a brown colour the pharmaceutical preparation.

It is important to note that the use of arginine or lysine salts of Ibuprofen (U.S. Pat. No. 4,279,926—SPA) is not suitable in the preparation of effervescent compositions because it does not result in a complete solubilization of the Ibuprofen (see example 7).

Moreover, it is important to underline that, without monosodium tartrate and bicarbonate, there is no aqueous solubilization of the Ibuprofen-arginine mixture under conditions suitable for the pharmaceutical applications. Likewise the monosodium tartrate-bicarbonate system is not able to dissolve Ibuprofen in water in the absence of arginine.

The compositions according to the present invention, on the contrary, are completely soluble in a short period of time, they show a very good tolerability on the level of both oral and gastric mucosa and moreover they allow a faster absorption of Ibuprofen with a consequently faster analgesic effect.

The increase of the absorption rate was estimated by evalutation of plasma concentrations after oral administering of aqueous solutions of effervescent tablets according to the present invention containing 200 mg of Ibuprofen and after oral administering of Ibuprofen commercial tablets with the same amount of active ingredient (see example 8).

The analysis of plasma concentration/time curve showed a remarkable anticipation of the peak time, a significant decrease of lag time and an increase of the mean plasma concentration (C max). The other pharmacokinetic parameters (AUC, distribution volume, total clearance) are substantially the same.

The analgesic effect of the preparation object of the present invention ends after a period of time from the administration substantially equal to that of Ibuprofen commercial solid preparations. Therefore, the analgesic effect begins in advance and it lasts for a longer period of time.

Some specific examples of the compositions according to the present invention are the following (percentage in weight):

(a)
Ibuprofen 9.59%
Arginine 18.47%
NaHCO$_2$ 33.57%
Sodium bitartrate 38.37%

(b)
Ibuprofen 9.59%
Arginine 12.00%
Lysine 6.47%
NaHCO$_3$33.57%

Sodium bitartrate 38.37%
(c)
  Ibuprofen 11.87%
  Arginine 22.84%
  NaHCO$_3$ 29.67%
  Sodium bitartrate 35.62%
(d)
  Ibuprofen 11.87%
  Arginine 19.84%
  Lysine 3.00%
  KHCO$_3$ 29.67%
  Sodium bitartrate 36.62%
(e)
  Ibuprofen 13.47%
  Arginine 25.92%
  NaHCO$_3$ 26.94%
  Sodium bitartrate 33.67%
(f)
  Ibuprofen 16.88%
  Arginine 32.49%
  NaHCO$_3$ 21.09%
  Sodium bitartrate 29.54%

For practical uses, the compositions object of the present invention are prepared in the form of an effervescent tablet or of an effervescent granulate.

Preferably every single effervescent tablet contains an effective amount of Ibuprofen that, according to the usual procedure, is 200 or 400 mg.

Likewise the granulate is preferably packed in bags each containing an amount of composition corresponding to 200 or 400 mg of Ibuprofen.

The preparation of the effervescent tablets or granulates needs that additives for pharmaceutical use are added to the composition.

The choice of such additives and their amount may vary according to the dosage form of the preparation (tablet or granulate) but both pharmaceutical preparations have a sweetener and a flavouring agent.

The sweetener may be a sugar (sacharose, fructose, sorbitol, lactose and so on), an artificial sweetener (saccharin, cyclamates, aspartame and so on) or their mixtures.

Some pharmaceutically acceptable dyes may be added to both pharmaceutical preparations.

The effervescent tablets may also contain a binder and a lubricant (magnesium stearate, polyethylene glycol, silica, fatty acids, castor oil, sodium benzoate) in order to facilitate the extruding of the tablet from the dies.

The preparation of the effervescent tablets or granulates is carried out according to usual procedures.

In order to better illustrate the present invention without limiting it, the following examples are now given.

EXAMPLE 1

Sieved Ibuprofen (200 g) and arginine (220 g) are put into a mixer. A hot aqueous solution of sweetener consisting of saccharose (335 g), lactose (450 g) and sodium saccharin (30 g) is added to them. The whole mixture is mixed and dried in oven.

The obtained granulates is milled by mill and then arginine (165 g), sodium bicarbonate (700 g), monosodium tartrate (800 g) and mint flavour (100 g) are added to it and mixed.

Amounts of 3 g of the obtained mixture are pressed in circular dies with 25 mm diameter giving effervescent tablets with the following composition:

Ibuprofen 200 mg
Arginine 385 mg
NaHCO$_3$ 700 mg
Sodium bitartrate 800 mg
Saccharose 335 mg
Lactose 450 mg
Sodium saccharin 30 mg
Mint flavour 100 mg By operating according to the procedure above described, effervescent tablets (3 g weight, 25 mm diameter) are prepared in which NaHCO$_3$ is substituted by an equal amount of KHCO$_3$.

EXAMPLE 2

The effervescent tablets of Example 1 were also prepared according to the following procedure.

Ibuprofen (200 g) and arginine (385 g) were wet granulated and the dried granulate was additioned and admixed with sodium bicarbonate (700 g) and sodium bitartrate (800 g).

Saccharose (335 g), lactose (450 g), sodium saccharin (30 g) and mint flavour (100 g) were added to the above reported composition. Amounts of 3 g of the obtained mixture were pressed in circular dies with 25 mm diameter giving effervescent tablets.

EXAMPLE 3

By working in a way similar to that described in example 1 effervescent tablets (1.625 g weight; 18 mm diameter) with the following composition are prepared:

Ibuprofen 200 mg
Arginine 385 mg
NaHCO$_3$ 400 mg
Sodium bitartrate 500 mg
Aspartame 40 mg
Anise flavour 100 mg Alternatively, amounts of 1.625 g of the mixture are distributed in paper-aluminum-polythene bags instead of being pressed.

EXAMPLE 4

By working in a way similar to that described in example 1 effervescent tablets (3.54 g weight; 25 mm diameter) with the following composition are prepared:

Ibuprofen 400 mg
Arginine 770 mg
NaHCO$_3$ 1000 mg
Sodium bitartrate 1200 mg
Aspartame 40 mg
Mint flavour 100 mg
Cupric chlorophyll 30 mg

EXAMPLE 5

By working in a way similar to that described in example 1 effervescent tablets (2.5 g weight; 22 mm diameter) with the following composition are prepared:

Ibuprofen 400 mg
Arginine 770 mg
NaHCO$_3$ 500 mg
Sodium bitartrate 700 mg
Aspartame 40 mg
Anise flavour 90 mg Alternatively, amounts of 2.5 g of the mixture are distirbuted in paper-aluminum-polythene bags instead of being pressed.

EXAMPLE 6

By operating according to the procedure described in Example 1, effervescent tablets (3 g weight, 25 mm diameter) were prepared having the same qualitative and quantitative composition as that of Example 1 (herein after referred as Composition 1) except for the fact that sodium bitartrate was replaced by an identical amount of the following acids:

Citric acid (Reference composition A)
Citric acid mono sodium salt (Reference composition B)
Citric acid disodium salt (Reference composition C)
Tartaric acid (Reference composition D)
Fumaric acid (Reference composition E)
Succinic acid (Reference composition F)
Malic acid (Reference composition G)
Adipic acid (Reference composition H)

The tablets corresponding to Composition 1 and Reference composition A to H were added to 100 ml of water at the temperature of 20° C. according to British Pharmacopeia 1980.

After disintegregation of the effervescent tablets the presence and the amount of precipitate (Ibuprofen) was evaluated.

Composition 1 gave a solution and no precipitate was observed. All the composition from A to H showed a visible and noticeable amount of precipitate.

The presence of the precipitate makes unacceptable the preparation both for the taste and for the local tolerability.

EXAMPLE 7

By operating according to the procedure described in Example 1, an effervescent tablet (3 g weight, 25 mm diameter) was prepared having the following composition (Reference I):

2-(4-isobutyl-phenyl)-propionate of arginine(*) 369 mg
NaHCO$_3$ 700 mg
Sodium bitartrate 800 mg
Saccharose 551 mg
Lactose 450 mg
Sodium saccharin 30 mg
Mint Flavour 100 mg (*)=salt of Ibuprofen with arginine corresponding to 200 mg of Ibuprofen.

The reference tablet (I) was added to 100 ml of water at 20° C. After disintegregation of the effervescent tablet the formation of a precipitate (Ibuprofen) could be observed.

EXAMPLE 8

Aqueous solutions (100 ml) of the effervescent tablets described in example 1 containing 200 mg of Ibuprofen (treatment A) and Ibuprofen commercial tablets containing the same amount of active ingredient (treatment B), were administered with a single oral dose to 12 subjects aged 35.8±2.03 years.

Each subject was apparently healthy, in particular as far as the renal, hepatic and hematopoietic function are concerned.

For the experiment a "cross-over" design was adopted: each subject received both preparations in two treatment sessions carried out 2 weeks apart, randomizing the order of administration.

During each of the two sessions, basal sample of venous blood were drawn (in the morning) from each fasting subject, prior to oral administration of the preparation A or B. Further venous blood samples were also collected 15, 30, 60, 90, 120, 240, 360 and 480 minutes after treatment.

The analytical determination of Ibuprofen in the blood samples was carried out following the HPLC method hereinafter described. Chromatographic conditions:

Apparatus: JASCO BIP-1 with UV detector UVIDEC 100-V
Mobil phase: CH$_3$CN:tetrabutylammonium hydroxide 0.005M (corrected to pH 7 with H$_3$PO$_4$ (38:62)
Flow: 2 ml/min
Wavelength: 225 mm
Internal standard: a solution in acetonitrile of ethyl p-hydroxybenzoate 0.0048M 5 µl of internal standard were added to 0.1 ml of blood. The whole was mixed and 1 ml of mobil phase was added to it.

The organic phase was extracted and allowed to rest. After 30 minutes it was centrifuged at 4000 rpm and filtered through a 0.45 µm filter.

20 µl of the filtrate were injected into the chromatograph. Under the described operative conditions the retention times were as follows:

Internal standard RT=4.5 minutes
Ibuprofen RT=5.5 minutes

The obtained results were reported in the following table.

TABLE 1

Mean plasma concentration of Ibuprofen after oral treatment with solution of effervescent tablets according to the present invention (treatment A) and after oral treatment with commercial Ibuprofen tablets (treatment B). Administered dose 200 mg of active ingredient.

| Treatment | Ibuprofen plasma concentration (µg/ml) time after treatment (minutes) | | | | | | | |
|---|---|---|---|---|---|---|---|---|
| | 15 | 30 | 60 | 90 | 120 | 240 | 360 | 480 |
| A | 29.1 | 22.7 | 16.5 | 13.0 | 10.4 | 4.9 | 2.2 | 1.1 |
| B | 3.4 | 12.9 | 16.8 | 15.4 | 13.3 | 5.8 | 3.1 | 1.9 |

Bioavailability parameters

The following parameters were calculated and evaluated.

The area under the curve of Ibuprofen plasma concentration from time "zero" to time 480 minutes (ACU obs=AUC$_{o \rightarrow 480}$) expressed as µg×h×ml$^{-1}$ was calculated following the "trapezoidal rule" method (Gibaldi M. and Perrier D., "Pharmacokinetics", pages 293-296, Marcel Dekker Inc., New York 1975).

The area under curve of Ibuprofen plasma concentration from time "zero" to "infinite" (AUC$_{tot \rightarrow \infty}$) was calculated by the following formula:

$$AUC_{0 \rightarrow 480} + AUC_{480 \rightarrow \infty}$$

where $$AUC_{480 \rightarrow \infty} = \frac{conc.\ 480\ min}{Ke^{(a)}}$$

(a) Ke=elimination constant.

The mean peak expressed in minutes was obtained by averaging the individual peak times.

The mean plasma peak (C max) expressed as µg/ml was calculated by averaging the single peak values of the concentrations.

Lag time (minutes): is the delay between the drug administration and the beginning of absorption.

The values of the above specified bioavailability parameters are reported in the following table.

TABLE 2

Pharmacokinetic parameters obtained after oral treatment with solution of Ibuprofen effervescent tablets (preparation A) and with Ibuprofen commercial tablets (preparation B). Administered dose: 200 mg of active ingredient.

| Analyzed parameter | Preparation A | Preparation B |
|---|---|---|
| AUC obs ($\mu g \times h \times ml^{-1}$) | 3295.5 | 3445.8 |
| AUC tot ($\mu g \times h \times ml^{-1}$) | 3689.7 | 3844.0 |
| Peak time (min.) | 15.0 | 67.5 |
| Plasma concentration C max ($\mu g/ml$) | 29.1 | 19.4 |
| Lag time (min.) | 0.0 | 10.24 |

What we claim is:

1. Pharmaceutical composition with analgesic activity consisting of
   Ibuprofen 9–17% w/w
   Arginine 17–33% w/w
   Sodium or potassium bicarbonate 20–35% w/w
   Sodium bitartrate 25–40% w/w
   the whole being 100%.

2. Pharmaceutical composition according to claim 1 in which the weight ratio between Ibuprofen and arginine is 1:1.9.

3. Pharmaceutical composition according to claim 1 in which an amount up to 40% of arginine, is substituted by lysine.

4. A composition according to claim 1 consisting of
   Ibuprofen 9.59%
   Arginine 18.47%
   NaHCO$_3$ 33.57%
   Sodium bitartrate 38.37%.

5. A composition according to claim 1 consisting of
   Ibuprofen 11.87%
   Arginine 22.84%
   NaHCO$_3$ 29.67%
   Sodium bitartrate 35.62%.

6. A composition according to claim 1 consisting of
   Ibuprofen 13.47%
   Arginine 25.92%
   NaHCO$_3$ 26.94%
   Sodium bitartrate 33.67%.

7. A composition according to claim 1 consisting of
   Ibuprofen 16.88%
   Arginine 32.49%
   NaHCO$_3$ 21.09%
   Sodium bitartrate 29.54%.

8. A pharmaceutical composition according to claim 3 consisting of
   Ibuprofen 9.59%
   Arginine 12.00%
   Lysine 6.47%
   NaHCO$_3$ 33.57%
   Sodium bitartrate 38.37%.

9. A pharmaceutical composition according to claim 3 consisting of
   Ibuprofen 11.87%
   Arginine 19.84%
   Lysine 3.00%
   KHCO$_3$ 29.67%
   Sodium bitartrate 35.62%.

10. A pharmaceutical preparation in the form of an effervescent tablet or granulate containing a composition according to claim 1.

11. A pharmaceutical preparation according to claim 10 containing also a sweetener and a flavouring agent and, optionally, a dye and a lubricant.

12. A pharmaceutical preparation in the form of an effervescent tablet containing an amount of effervescent composition according to claim 1 corresponding to 200 mg or 400 mg of Ibuprofen each tablet.

13. An effervescent granulate containing an amount of effervescent composition according to claim 1 corresponding to 200 or 400 mg of Ibuprofen each single dose form.

14. An effervescent tablet according to claim 10 consisting of
    Ibuprofen 200 mg
    Arginine 385 mg
    NaHCO$_3$ 700 mg
    Sodium bitartrate 800 mg
    Saccharose 335 mg
    Lactose 450 mg
    Sodium saccharin 30 mg
    Flavour 100 mg.

15. An effervescent tablet according to claim 10 consisting of
    Ibuprofen 200 mg
    Arginine 385 mg
    NaHCO$_3$ 400 mg
    Sodium bitartrate 500 mg
    Aspartame 40 mg
    Flavour 100 mg.

16. An effervescent tablet according to claim 10 consisting of
    Ibuprofen 400 mg
    Arginine 770 mg
    NaHCO$_3$ 1000 mg
    Sodium bitartrate 1200 mg
    Aspartame 40 mg
    Flavour 100 mg
    Colourant 30 mg.

17. An effervescent tablet according to claim 10 consisting of
    Ibuprofen 400 mg
    Arginine 770 mg
    NaHCO$_3$ 500 mg
    Sodium Bitartrate 700 mg
    Aspartame 40 mg
    Flavour 90 mg.

18. An effervescent granulate according to claim 10 consisting of
    Ibuprofen 200 mg
    Arginine 385 mg
    NaHCO$_3$ 400 mg
    Sodium bitartrate 500 mg
    Aspartame 40 mg
    Flavour 100 mg.

19. An effervescent granulate to claim 10 consisting of
    Ibuprofen 400 mg
    Arginine 770 mg
    NaHCO$_3$ 1000 mg
    Sodium bitartrate 1200 mg
    Aspartame 40 mg
    Flavour 100 mg
    Colourant 30 mg.

20. A method for producing analgesia consisting of administering to a subject a pharmaceutical preparation containing a composition according to claim 1.

21. A method for producing analgesia consisting of administering to a subject a pharmaceutical preparation according to claim 10.

* * * * *